United States Patent [19]

Walshe

[11] Patent Number: 5,733,887
[45] Date of Patent: Mar. 31, 1998

[54] ANTIPARASITIC AGENTS

[75] Inventor: Nigel Derek Walshe, Sandwich, United Kingdom

[73] Assignee: Pfizer Inc., New York, N.Y.

[21] Appl. No.: 553,692

[22] PCT Filed: Jun. 8, 1994

[86] PCT No.: PCT/EP94/01905

§ 371 Date: Nov. 20, 1995

§ 102(e) Date: Nov. 20, 1995

[87] PCT Pub. No.: WO94/29328

PCT Pub. Date: Dec. 22, 1994

[30] Foreign Application Priority Data

Jun. 12, 1993 [GB] United Kingdom ............... 9312154

[51] Int. Cl.$^6$ .............. A61K 31/70; A61K 31/335
[52] U.S. Cl. .................. 514/28; 514/450; 536/7.1; 549/450
[58] Field of Search .............. 514/450, 28; 549/264; 536/7.1

[56] References Cited

FOREIGN PATENT DOCUMENTS

| | | | |
|---|---|---|---|
| 303933 | 2/1989 | European Pat. Off. | ...... C07D 493/22 |
| 327270 | 8/1989 | European Pat. Off. | . |
| 340849 | 11/1989 | European Pat. Off. | . |
| 501026 | 9/1992 | European Pat. Off. | ...... A01N 43/90 |
| 9318041 | 9/1993 | WIPO | . |

OTHER PUBLICATIONS

Davies et al., Chem. Soc. Rev., 20, pp. 271–339 (1991).
Patent Abstracts of Japan, vol. 12, No. 263 (C-514) (1988).

*Primary Examiner*—Amelia Owens
*Attorney, Agent, or Firm*—Peter C. Richardson; Paul H. Ginsburg; Gezina Holtrust

[57] ABSTRACT

Antiparasitic compounds of the formula (I)

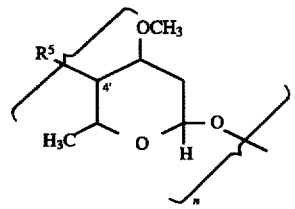

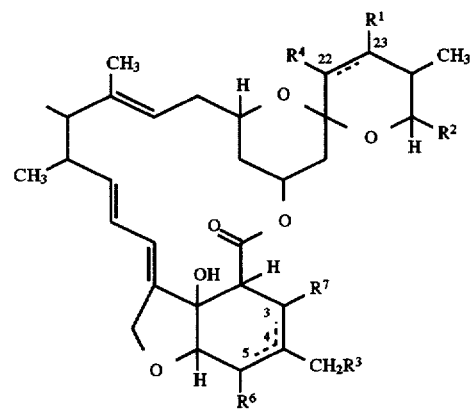

(I)

where the broken lines between the 3–4 and 4–5 positions represent optional bonds and either (i) the 3–4 optional bond is present; the 4–5 optional bond is absent, $R^7$ is absent and $R^6$ is halogen atom, an isothiocyanate group, a diazo group, a thioureido group of formula $NHCSNR^{15}R^{16}$ where $R^{15}$ and $R^{16}$ are independently H, $C_1$–$C_8$ alkyl, cycloalkyl, aryl or aralkyl groups, an azido group or a $C_1$–$C_8$ alkylcarbonylthio group, or (ii) the 4–5 optional bond is present, the 3–4 optional bond is absent, $R^6$ is absent and $R^7$ is a mercapto, $C_1$–$C_8$ alkylthio, oxo, optionally substituted oximino or $C_1$–$C_8$ alkylcarbonylthio group; or $R^7$ is absent and $R^6$ is CN, with the provisos that the compounds where $R^6$ is α-fluoro and $R^2$ is $CH(CH_3)_2$, $CH(CH_3)C_2H_5$, $C(CH_3)=CHCH_3$, $C(CH_3)=CHC_2H_5$ and $C(CH_3)=CHCH(CH_3)_2$ are excluded.

16 Claims, No Drawings

ANTIPARASITIC AGENTS

This invention relates to new antiparasitic agents, related to the milbemycins and avermectins and to processes for their preparation and compositions thereof.

The avermectins are a group of broad spectrum antiparasitic agents referred to previously as the C-076 compounds. They are produced by fermenting a strain of the microorganism *Streptomyces avermitilis* under aerobic conditions in an aqueous nutrient medium containing inorganic salts and assimilable sources of carbon and nitrogen. The isolation and the chemical structure of the eight individual components which make up the C-076 complex is described in detail in British Patent Specification 1573955.

The C-076 complex comprises eight distinct but closely related compounds described as C-076 A1a, A1b, A2a, A2b, B1a, B1b, B2a and B2b. The "a" series of compounds refers to the natural avermectins wherein the 25-substituent is (S)-sec-butyl and the "b" series to those wherein the 25-substituent is isopropyl. The designations "A" and "B" refer to avermectins wherein the 5-substituent is methoxy or hydroxy, respectively, and the numeral "1" refers to avermectins wherein a double bond is present at the 22-23 position, and numeral "2" to avermectins lacking the 22-23 double bond and having a hydrogen at the 22-position and hydroxy at the 23 position.

In our European Patent Applications 0214731, 0284176, 0317148, 0308145, 0340832, 0335541 and 0350187 there are described preparations of compounds related to the avermectins but having a group at the 25-position other than the isopropyl or (S)-sec-butyl groups found in the original avermectin compounds disclosed in British Patent Specification 1573955. Such compounds may be prepared by fermentation of particular strains of *Streptomyces avermitilis* in the presence of organic acids or derivatives thereof. Production of such avermectins is described in Journal of Antibiotics (1991), 44, No. 3, pp 357–365.

The milbemycins form another group of related macrolides which are distinguished from the avermectins in lacking a sugar residue attached at the C-13 position. Examples of such compounds are described in UK patent 1390336, and European patent publications 170006, 254583, 334484 and 410615. In addition to these fermentation products a large number of publications describe compounds derived semisynthetically from these fermentation products many of which possess useful antiparasitic activities. Some of this chemistry is reviewed in *Macrolide Antibiotics*, Omura S., Ed., Academic press, New York (1984) and by Davies, H. G., Green, R. H. in *Natural product Reports* (1986), 3, 87–121 and in Chem. Soc. Rev., 1991, 20, 271–339.

European Patent Application 340 849 discloses fluoro-avermectin and fluoromilbemycin compounds with the fluorine residing on at least one of the 4a, 5 or 4" positions, and arising from displacement of hydroxy or hydroxy-derived substituents. With regard to the synthesis of the 5-fluoro compounds, the chemistry disclosed therein results in the exclusive formation of the 5-α-fluoro compounds, and none of the 5-β-diastereomers.

It has been found that certain compounds synthetically derivable from known avermectins and avermectin derivatives possess unexpected beneficial biological properties.

According to one aspect of the invention there are provided compounds of formula (I):

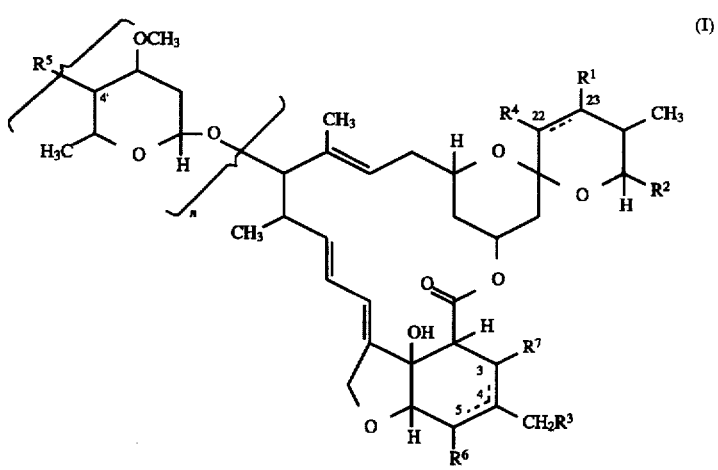

wherein the broken line at the 22–23 position represents an optional bond and either this bond is present and $R^1$ and $R^4$ are absent or this bond is absent and $R^1$ and $R^4$ are independently H, $OR^8$ wherein $R^8$ is H, $C_1$–$C_8$ alkyl, $C_1$–$C_8$ alkenyl, aralkyl, $C_2$–$C_8$ alkanoyl, $C_3$–$C_8$ alkenoyl, aralkanoyl, aroyl, optionally substituted carbamoyl, optionally substituted methylene, oxo or optionally O-substituted oximino;

$R^2$ is:

(a) an alpha-branched $C_3$–$C_8$ alkyl, alkenyl, alkoxyalkyl, or alkylthioalkyl group; an alpha-branched $C_4$–$C_8$ alkynyl group; a ($C_5$–$C_8$ cycloalkyl)alkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or (b) a group of the formula —$CH_2R^9$ wherein $R^9$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group, wherein any of said alkyl, alkoxy, alkenyl or alkynyl groups may be substituted by one or more halo atoms; or a $C_2$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or a group of the formula $SR^{10}$ wherein $R^{10}$ is $C_1$–$C_8$ alkyl, $C_2$–$C_8$ alkenyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo; or a 3 to 6 membered oxygen or sulphur containing heterocyclic ring which may be saturated, or fully or partially unsaturated and which may optionally be substituted by one or more $C_1$–$C_4$ alkyl groups or halo atoms; or (c) a $C_1$–$C_6$ alkyl group substituted by one oxo or one or more hydroxy groups or by a single oxygen atom on two adjacent carbon atoms forming an oxirane ring, or $R^2$ is a $C_1$–$C_5$ alkyl group substituted by a $C_1$–$C_6$ alkoxycarbonyl group, said substituents on $R^2$ being attached to either or both of a terminal carbon atom and a carbon atom adjacent a terminal carbon atom of $R^2$; or (d) $=CH_2$ or a group of the formula:

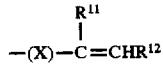

wherein $R^{11}$ and $R^{12}$ are both H; $R^{11}$ is H and $R^{12}$ is $C_1$–$C_8$ alkyl, or one of $R^{11}$ and $R^{12}$ is H and the other is phenyl, heteroaryl, $C_2$–$C_6$ alkoxycarbonyl or substituted phenyl or heteroaryl wherein said substituent is fluorine, chlorine, $C_1$–$C_4$ alkyl, $C_1$–$C_4$ alkoxy, $C_1$–$C_4$ alkylthio, hydroxy ($C_1$–$C_4$)alkyl, cyano, aminosulphonyl, $C_2$–$C_6$ alkanoyl, $C_2$–$C_6$ alkoxycarbonyl, nitro, trifluoromethyl, trifluoromethoxy, amino or mono or di-($C_1$–$C_4$ alkyl)amino; and X is a direct bond or is an alkylene group having from 2 to 6 carbon atoms which may be straight or branched-chain; or (e) phenyl which may optionally be substituted with at least one substituent selected from $C_1$–$C_4$ alkyl, $C_1$–$C_4$ alkoxy and $C_1$–$C_4$ alkylthio groups, halo atoms, trifluoromethyl, and cyano; or (f) $R^2$ may be a group of formula (II):

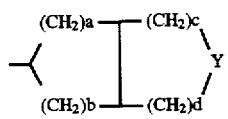

wherein Y is O, S or $-CH_2-$ and a, b, c and d may each independently be 0, 1 or 2; the sum of a, b, c and d not exceeding 5;

$R^3$ is H, $OR^8$ where $R^8$ is as defined above, or $R^3$ is a halogen atom;

n is 0, 1 or 2;

$R^5$ is attached by a single bond and is H, $OR^8$ where $R^8$ is as defined above, a halogen atom, amino, N-loweralkylamino, N,N-diloweralkylamino, N-loweralkanoylamino, N,N-diloweralkanoylamino, triloweralkylsilyloxy, $-S(O)_mR^{13}$ where m is 0, 1 or 2, or $-SCOR^{13}$ wherein $R^{13}$ is H or an optionally substituted $C_1$–$C_8$ alkyl, cycloalkyl or aryl group;

or $R^5$ is attached by a double bond and is oxo, or an optionally substituted oximino, semicarbazono, thiosemicarbazono or hydrazono group; or $R^5$ represents OH, $R^{14}$ both of which are attached by a single bond, $R^{14}$ being an optionally substituted $C_1$–$C_8$ alkyl, $C_2$–$C_8$ alkenyl or aryl group, the broken lines between the 3–4 and 4–5 positions represent optional bonds and either, (i) the 3–4 optional bond is present, the 4–5 optional bond is absent. $R^7$ is absent and $R^6$ is a halogen atom, an isothiocyanate group, a diazo group, a thioureido group of formula $NHCSNR^{16}R^{16}$ where $R^{15}$ and $R^{16}$ are independently H, $C_1$–$C_8$ alkyl, cycloalkyl, aryl or aralkyl groups, an azido group or a $C_1$–$C_8$ alkylcarbonyl-thio group, or (ii) the 4–5 optional bond is present, the 3–4 optional bond is absent, $R^6$ is absent and $R^7$ is a mercapto, $C_1$–$C_8$ alkylthio, oxo, optionally substituted oximino or $C_1$–$C_8$ alkylcarbonylthio group; or $R^7$ is absent and $R^6$ is CN;

with the provisos that:

(a) when $R^8$ represents $\alpha$-fluoro; then $R^2$ does not represent $CH(CH_3)_2$, $CH(CH_3)(C_2H_5)$, $C(CH_3)=CH(CH_3)$, $C(CH_3)=CH(C_2H_5)$ or $C(CH_3)=CHCH(CH_3)_2$;

(b) when $R^1$ end $R^4$ each represent H; $R^2$ represents $CH(CH_3)(C_2H_5)$; $R^3$ represents H; $R^5$ represents OH; and $R^6$ represents $\alpha$-Cl or $\alpha$-Br; then n does not represent 2; and (c) when $R^1$ represents H or OH; $R^2$ represents $C(CH_3)=CHCH(CH_3)_2$; $R^3$, $R^4$ and $R^5$ each represent H; and $R^6$ represents $\alpha$-Cl; then n does not represent 0.

The oximino, semicarbazono, thiosemicarbazono or hydrazono groups may be substituted by a wide variety of substituents including $C_1$–$C_8$ alkyl, alkenyl, alkynyl, trialkylsilyl and aralkyl groups which may themselves be substituted by halo, carboxy and/or other groups. The methylene groups may be substituted by a $C_1$–$C_8$ alkyl group cyano or by an aryl group.

Unless the context otherwise requires, all alkyl, alkenyl and alkynyl substituents having 3 or more carbon atoms may be straight or branched-chain and halogen atoms may be F, Cl, Br or I.

The term "aryl" includes phenyl which may be substituted by at least one $C_1$–$C_6$ alkyl, hydroxy, $C_1$–$C_6$ alkoxy, halo, nitro or $CF_3$ group.

In the present invention the term "loweralkyl" is intended to indicate those alkyl groups of from 1 to 6 carbon atoms such as methyl, ethyl, propyl, isopropyl, butyl, pentyl, hexyl, and the like, either straight or branched chain.

The term "loweralkoxy" is intended to include those alkoxy groups of from 1 to 8 carbon atoms such as methoxy, ethoxy, propoxy, isopropoxy, butoxy, pentoxy, hexoxy, heptoxy, octoxy, and the like, either straight or branched chain, and linked at any point in the chain.

The term "loweralkanoyl" is intended to include those alkanoyl groups of from 1 to 6 carbon atoms such as formyl, acetyl, propionyl, buytryl, pentanoyl, hexanoyl, and the like.

The above structural formula is shown without a definitive stereochemistry. However, during the course of the synthetic procedures used to prepare such compounds, the products of such procedures can be a mixture of stereoisomers. In particular, the stereoisomers at the 3, 4',4",5, 13, 22 and 23-positions may be oriented either $\alpha$- or $\beta$-representing such groups being below or above the general plane of the molecule, respectively. In each of such case both the $\alpha$- and $\beta$-configurations are intended to be included within the ambit of this invention, with the exception of the 5-$\alpha$-fluoro compounds described earlier (EP-A-340849).

Compounds according to the invention include those in which $R'$ is OH, the 22–23 optional bond is present or absent, $R^4$ is H, $R^1$ is H, OH or $O(C_1$–$C_4$ alkyl) and $R^3$ is H. $R^2$ may be branched alkyl or cycloalkyl. Compounds in which $R^6$ is β-halo, especially β-fluoro, are preferred. Compounds within the range of this invention are both safe and have unexpectedly high potent systemic activity against fleas and other important arthropod parasites of cats and dogs. Individual compounds are identified in the Examples below.

A wide variety of avermectin and milbemycin derivatives are available by treating the diazo compounds (Ia, $R^6=N_2$, 3,4 optional bond present) with nucleophilic species.

The diazo compounds of formula (Ia) may be prepared from the corresponding 5-keto avermectin or milbemycin derivatives, which may themselves be prepared in known manner by oxidation of the known 5-hydroxy avermectin or milbemycin derivatives using manganese dioxide. The 5-keto compound may be allowed to react with hydrazine, for example by treatment with hydrazine hydrochloride and acetic acid in a dichloromethane solvent at a low

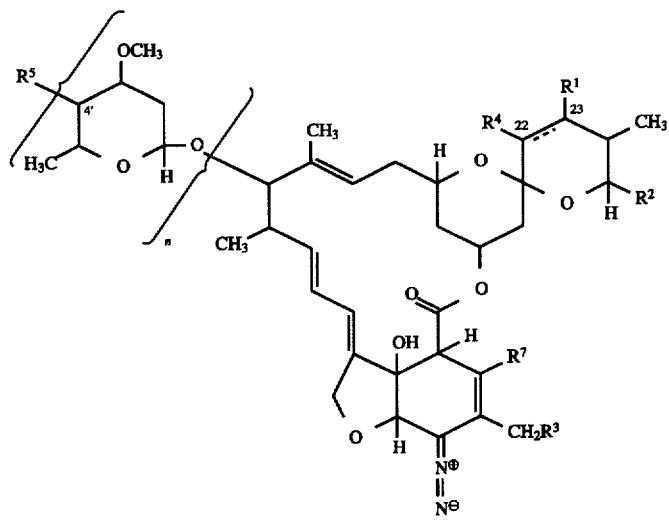

(Ia)

where n and $R^1$–$R^5$ are as defined above, with an appropriate nucleophilic reagent, generally in an inert solvent such as diethyl ether or toluene to replace the diazo group with a nucleophilic group. The nucleophilic reagent may be an acidic compound, such as hydrogen sulphide or a mercaptan to give a compound of formula (I) having a —SH or —S($C_1$–$C_8$ alkyl) substituent, a thiolcarboxylic acid to give an alkylcarbonylthio substituent or hydrazoic acid to give an azido substituent, or thiocyanic acid to give an isothiocyanato substituent or HF or HCl to give a fluoro or chloro substituent. Depending on the identity of the nucleophilic group, substitution may occur at either or both of the 3- and 5-positions. It has been found that hydrogen sulphide or a mercaptan gives predominantly a 3-mercapto or 3-alkylthio compound, HCl, HF and HNCS give predominantly a 5-chloro, 5-fluoro or 5-isothiocyanato compound, and an alkylcarbonylthio acid gives a mixture of 3- and 5-alkylcarbonylthio compounds. The 5-isothiocyanato compounds may be converted to the corresponding thioureido compounds by reaction with ammonia or the appropriate amine.

Replacement of the diazo group by a nucleophilic group generally results in a mixture of 3- or 5- α and β isomers and these may be separated by conventional methods such as chromatography. This process allows preparation of stereoisomers of avermectin derivatives which are not obtainable by known methods.

For example the present process allows preparation of 5-β-chloro and β-fluoro derivatives of avermectins whereas replacement of a 5-hydroxy group of an avermectin derivative with chloro or fluoro by hitherto known methods produces only the 5-α derivative.

It has been found that treatment of a diazo compound of formula (Ia) with cuprous cyanide in a polar solvent such as acetonitrile gives a compound of formula (I) in which the double bond is present between the 4 and 5 positions and a cyanide group is present at the 5 position.

temperature, to give a 5-hydrazono derivative which is then oxidised with manganese dioxide at low temperatures to yield the desired 5-diazo derivative. The reaction steps are shown schematically as follows:

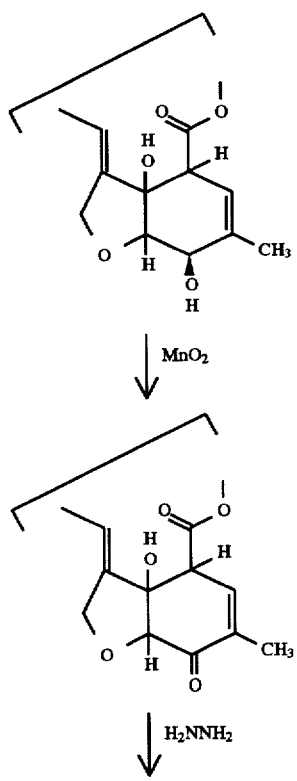

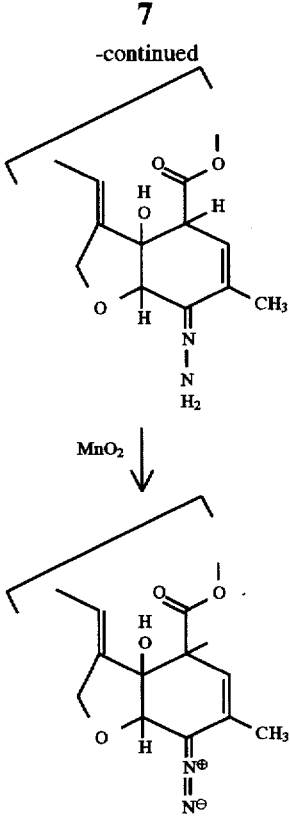

It has unexpectedly been found that the 5-diazo avermectin and milbemycin derivatives are stable in the pure state and capable of storage for extended period at ambient temperatures; also they are readily prepared in high yield by the procedure described above. These results are surprising, since cyclic diazoalkanes conjugated to a double bond are described in the literature as highly unstable. No natural product has ever had this functional group introduced.

The diazo compounds of formula (Ia) may be prepared as described above from the 5-keto compounds having substituents $R^1$–$R^5$ which are not affected by the reagents used during the reaction with hydrazine and subsequent oxidation. Any substituents likely to be affected during oxidation may be protected and subsequently deprotected by known methods. Compounds having keto groups in substituents $R^1$–$R^5$ cannot generally be used as starting compounds as hydrazine will react with these keto groups also. Compounds of formula (I) having a keto group in substituents $R^1$–$R^5$ may generally be prepared by oxidation of appropriate hydroxy groups in these substituents after conversion of the diazo compound of formula (Ia) to the compound of formula (I).

The 5-hydroxy avermectin or milbemycin derivatives used as starting materials for the above-described syntheses are either known materials or may be made from known materials by synthetic steps known in the art.

Further synthetic steps to modify the $R^1$–$R^5$ groups may be carried out after conversion of the diazo compounds to further compounds of formula (I). These synthetic steps may require sequential reactions at the 4',4", 13, 22, 23 and 25 positions of the molecule, using protecting groups as necessary, and the exact order in which these reactions are carried out may vary. The steps required for these conversions are described in the prior art documents mentioned above.

The compounds of formula I as defined above, but without provisos (b) and (c), are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example: Dirofilaria, in dogs and various parasites which can infest livestock, companion animals such as cats and dogs and also humans including gastro-intestinal parasites such as Ancylostoma, Necator, Ascaris, Strongyloides, Trichinella, Capillaria, Toxocara, Toxascaris, Trichuris, Enterobius and parasites which are found in the blood or other tissues and organs such as filarial worms and the extra intestinal stages of Strongyloides, Toxocara and Trichinella.

The compounds are also of particular value in treating ectoparasite infections including particular arthropod ectoparasites of humans, animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against arthropod pests of stored grain and of agricultural plants such as spider mites, aphids, caterpillars and against migratory orthopterans such as locusts. We have discovered that compounds within the scope of this invention are both safe and have unexpectedly high patent systemic activity against fleas and other important arthropod parasites of cats and dogs.

The compounds of formula I, as defined above, but without provisos (b) and (c), may be administered as a formulation appropriate to the specific use envisaged and to the particular species of host animal being treated and the parasite or insect involved. For use as an anthelmintic the compounds may be administered by injection, either subcutaneously or intramuscularly, alternatively they may be administered orally in the form of a capsule, bolus, tablet, chewable tablet or liquid drench, or they may be administered as a topical formulation or as an implant. For topical application dip, spray, powder, dust, pour-on, spot-on, jetting fluid, shampoos, collar, tag or harness may be used. Such formulations are prepared in a conventional manner in accordance with standard veterinary practice. Thus capsules, boluses or tablets may be prepared by mixing the active ingredient with a suitable finely divided diluent or carrier, additionally containing a disintegrating agent and/or binder such as starch, lactose, talc, or magnesium stearate. A drench formulation may be prepared by dispersing the active ingredient in an aqueous solution together with dispersing or wetting agents and injectable formulations may be prepared in the form of a sterile solution or emulsion. Pour-on or spot-on formulations may be prepared by dissolving the active ingredient in an acceptable liquid carrier vehicle, such as butyl digol, liquid paraffin or non-volatile ester with or without addition of a volatile component such as isopropanol. Alternatively, pour-on, spot-on or spray formulations can be prepared by encapsulation to leave a residue of active agent on the surface of the animal. These formulations will vary with regard to the weight of active compound depending on the species of host animal to be treated, the severity and type of infection and the body weight of the host. The compounds may be administered continuously, particularly for prophylaxis, by known methods. Generally for oral, parenteral and pour-on administration a dose of from about 0.001 to 10 mg per kg of animal body weight given as a single dose or in divided doses for a period of from 1 to 5 days will be satisfactory but of course there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests the compounds are applied as sprays, dusts, pour-on formulations, emulsions and the like in accordance with standard agricultural practice.

For human use the compounds are administered as a pharmaceutically acceptable formulation in accordance with normal medical practice.

The preparation of compounds according to the invention are illustrated by the following Examples in which "tlc" means thin layer chromatography.

EXAMPLE 1

5-Keto-25-cyclohexylavermectin B2 ($R^1$=OH, $R^2$=cyclohexyl, $R^3$=H, $R^4$=H, $R^5$=OH, n=2)

25-Cyclohexylavermectin B2 (10 g) (obtained according to EP 214 731) was suspended in a mixture of ether (450 ml) and tetrahydrofuran (50 ml). Activated manganese dioxide (25 g) was added portionwise over 4 hours whilst the mixture was stirred at room temperature. After 48 hours, further oxidant was added until reaction was judged to be completed by tlc. The suspension was then filtered through Hyflo (trade mark), the inorganic residue washed well with ether, and the combined filtrates evaporated to give the title compound (7.6 g) as a yellow foam, characterised by mass and nmr spectroscopy. Reverse phase high performance liquid chromatography analysis showed it to be 96.9% pure.

EXAMPLE 2

5-Hydrazono-25-cyclohexylavermectin B2

Hydrazine dihydrochloride (3 g) and sodium acetate (6 g) were stirred for 40 minutes in a mixture of dichloromethane (100 ml) and glacial acetic acid (2 ml). This mixture was then cooled in ice whilst 5-keto-25-cyclohexylavermectin B2 (1.5 g), from Example 1, was added. The reaction was then stirred for 5 hours, during which time it was allowed to reach room temperature, when tlc showed reaction to be complete.

The product was then washed with water (100 ml), and brine (100 ml), dried ($MgSO_4$), and evaporated to give the title compound (1.55 g), characterised by mass and nmr spectroscopy. Reverse-phase high performance liquid chromatography showed it to be 97.5% pure.

EXAMPLE 3

5-Diazo-25-cyclohexylavermectin B2

The 5-hydrazono-25-cyclohexylavermectin B2 (1.55 g), from Example 2, was dissolved in ether (250 ml) and the solution cooled to 0° C. Activated manganese dioxide (8 g) was added in portions over 10 minutes. The suspension was then stirred at 0° C. for 30 minutes, when tlc indicated reaction was complete. The reaction mixture was filtered through Hyflo (trade mark), and the inorganic residue washed well with ether (200 ml). The combined filtrates were evaporated to give the title compound (1.05 g) as a pink solid which was characterised by infra-red and nmr spectrochemistry. The infra-red spectrum has a strong band at about 2080 $cm^{-1}$, which is characteristic of the diazo linkage in this compound, and also the other diazo compounds herein exemplified. 1-D nmr spectroscopy showed signals characteristic of H-2, H-3 and H-6, and a characteristic cross-peak for H-2/H-3 coupling in the 2-D spectrum.

Again, these were also typical of all diazo compounds herein disclosed. Reverse-phase high performance liquid chromatographic analysis showed the title compound obtained in this way to be 99% pure.

EXAMPLE 4

5-β-Fluoro-25-cyclohexylavermectin B2 and its 5-α-diastereomer

5-Diazo-25-cyclohexylavermectin B2 (0.25 g), from Example 3, was dissolved in dry ether (20 ml) in a polypropylene tube. Pyridinium poly(hydrogen fluoride) (0.2 ml) was added and the mixture stirred at room temperature overnight. The solution was then washed twice with saturated sodium hydrogen carbonate solution, then with brine. It was dried over sodium sulphate and evaporated to dryness. The resulting yellow solid was then chromatographed over silica gel, eluting with ether and collecting the material with Rf of 0.25–0.35 on a TLC plate eluted with ether. This was then purified on a 2" Dynamax (trade mark) ODS hplc column, eluting at 45 ml/minute with water:methanol:acetonitrile 20:14:66 rising to 18:14:68 over 24 minutes, then isocratic for 29 minutes, then to 17:14:69. The material with retention time of 40 minutes was collected, and shown to be the title compound by mass and nmr spectroscopy. The 1-D nmr spectrum showed peaks characteristic of H-2, H-3, H-5 and H-6. Furthermore, the 2-D nmr spectrum showed highly characteristic cross-peak patterns for H-5/H-6, H-2/H-3, H-2/H-5, H-2/4-$CH_3$ and H-3/4-$CH_3$ couplings. The $^{19}F$ nmr spectrum, both proton-decoupled and proton-undecoupled showed characteristic shifts and proton couplings for the 5-β-fluorine. These were typical of all the 5-β-fluoro compounds herein exemplified.

The 5-α-diastereomer was collected from the silica gel chromatography in the fractions showing a spot of Rf 0.4 on a TLC plate eluted with ether. It was purified by hplc as before, being eluted after 60 mins, and characterised as above by $^1H$ and $^{19}F$ nmr, and mass spectroscopy.

EXAMPLE 5

5-β-Fluoro-25-cyclohexylavermectin B2 monosaccharide (n=1)

5-β-Fluoro-25-cyclohexylavermectin B2 (0.2 g), from Example 4, was dissolved in a mixture of isopropanol (5 ml) and concentrated sulphuric acid (50 uL). This was stirred overnight. The solution was then poured into excess saturated sodium hydrogen carbonate solution, and the product extracted into ether. The ether extracts were dried ($MgSO_4$) and evaporated. The product was purified on a 2"5µ Microsorb (trade mark) column, eluting with water:methanol:acetonitrile 21:14:63. Product eluted at 24–26 minutes, and was characterised by mass and nmr spectroscopy, as described in Example 4.

EXAMPLE 5a

5-α-Fluoro-25-cyclohexylavermectin B2 monosaccharide

5-α-Fluoro-25-cyclohexylavermectin B2 (0.2 g), from Example 4, was hydrolysed and purified in the same manner as described in Example 5. It was characterized by mass and nmr spectroscopy, as described in Example 4.

EXAMPLE 6

5-Hydrazono-22,23-dihydro-25-cyclohexylavermectin B1 monosaccharide ($R^1$=H, $R^2$=cyclohexyl, $R^3$=H, $R^4$=H, $R^5$=OH, n=1)

Hydrazine dihydrochloride (1.5 g) and sodium acetate (3 g) were stirred for 40 minutes in a mixture of dichloromethane (50 ml) and glacial acetic acid (1 ml). This mixture was then cooled in ice whilst 5-keto-22,23-dihydro-25-cyclohexylavermectin B1 monosaccharide (0.5 g) (Example 28A) was added. The reaction was then stirred for 5 hours, during which time it was allowed to reach room temperature, when tlc showed reaction to be complete. It was then washed with water (100 ml), and brine (100 ml), dried (MgSO$_4$), and evaporated to give the title compound (0.5 g), characterised by mass and nmr spectroscopy. Reverse-phase high performance liquid chromatography showed it to be 91% pure.

EXAMPLE 7

5-Diazo-22,23-dihydro-25-cyclohexylavermectin B1 monosaccharide.

The 5-hydrazono-22,23-dihydro-25-cyclohexylavermectin B1 monosaccharide (0.45 g) from Example 6, was dissolved in ether (60 ml) and the solution cooled to 0° C. Activated manganese dioxide (2 g) was added in portions over 10 minutes. The suspension was then stirred at 0° C. for 30 minutes, when tlc indicated reaction was complete. The reaction mixture was filtered through Hyflo (trade mark), and the inorganic residue washed well with ether. The combined filtrates were evaporated to give the title compound (0.4 g) as a pink solid, which was characterised by infra-red and nmr spectroscopy, as described in Example 3. Reverse-phase high performance liquid chromatographic analysis showed it to be 92% pure.

EXAMPLE 8

5-β-Fluoro-22,23-dihydro-25-cyclohexylavermectin B1 monosaccharide and its 5-α-diastereomer 5-Diazo-22,23-dihydro-25-cyclohexylavermectin B1 monosaccharide, from Example 7, (0.6 g) was dissolved in dry ether (20 ml) in a polypropylene tube. Pyridinium poly(hydrogen fluoride) (0.2 ml) was added and the mixture stirred at 0° overnight. The solution was then washed twice with saturated sodium hydrogen carbonate solution, then with brine. It was dried over magnesium sulphate and evaporated to dryness. The resulting yellow solid was then chromatographed over silica gel, eluting with ether. The 5-α-diastereomer eluted first, followed by its 5-β-isomer. Appropriate fractions were collected and pooled. The 5-β-diastereomer was then purified on a 1" Dynamax (trade mark) 5μ ODS hplc column, eluting at 20 ml/minute with water:methanol:acetonitrile 9:13:78. The material with retention time of 20–23 minutes was collected, and shown to be the 5-β-diastereomer by mass and nmr spectroscopy, as described in Example 4.

The 5-α-diastereomer was similarly purified (retention time 25–28 minutes). It was characterised by mass and nmr spectroscopy, as described in Example 4.

EXAMPLE 9

5-Hydrazono-25-cyclohexylavermectin B1 (R$^1$ and R$^4$ absent, double bond at 22–23 position, R$^2$=cyclohexyl, R$^3$=H, R$^5$=OH, n=2)

Hydrazine dihydrochloride (40 g) and sodium acetate (80 g) were stirred for 40 minutes in a mixture of dichloromethane (1000 ml) and glacial acetic acid (27 ml). This mixture was then cooled in ice whilst 5-keto-25-cyclohexylavermectin B1 (20 g) (prepared from 25-cyclohexyl avermectin B1 by the method of Example 1) was added. The reaction was then stirred for 5 hours, during which time it was allowed to reach room temperature, when tlc showed reaction to be complete. It was then washed with Water and brine, dried (MgSO$_4$), and evaporated to give the title compound (21 g), characterised by mass and nmr spectroscopy.

EXAMPLE 10

5-Diazo-25-cyclohexylavermectin B1

The 5-hydrazono-25-cyclohexylavermectin B1 (21 g), from Example 9, was dissolved in ether (1000 ml) and the solution cooled to 0° C. Activated manganese dioxide (80 g) was added in two 40 g lots at 30 minute intervals. The suspension was then stirred at 0° C. for 60 minutes, when tlc indicated reaction was complete. The reaction mixture was filtered through Hyflo (trade mark), and the inorganic residue washed well with ether. The combined filtrates were evaporated to give the title compound (17 g) as a pink solid, which was characterised by infra-red and nmr spectroscopy, as described in Example 3. Reverse-phase high performance liquid chromatographic analysis showed it to be 93% pure.

EXAMPLE 11

5-β-Fluoro-25-cyclohexylavermectin B1 and its 5-α-diastereomer

5-Diazo-25-cyclohexylavermectin B1 (15 g), from Example 10, was dissolved in dry ether (500 ml) in a polypropylene vessel. Pyridinium poly(hydrogen fluoride) (5 ml) was added and the mixture stirred at 0° overnight, and then at room temperature for 24 hours. The solution was then washed twice with saturated sodium hydrogen carbonate solution, then with brine. It was dried over sodium sulphate and evaporated to dryness to give a red foam. This was then chromatographed over silica gel (350 g), eluting with ether:hexane 1:1. The 5-β-diastereomer was collected in fractions with Rf of 0.4 on a TLC plate eluted with ether. This was then purified on a 2" Dynamax (trade mark) ODS hplc column, eluting at 45 ml/minute with water:methanol:acetonitrile 15:13:72. The material with retention time of 37–58 minutes was collected, and further purified on a 2"5μ Microsorb (trade mark) column. The product was shown to be the title compound by mass and nmr spectroscopy, as described in Example 4.

The 5-α-diastereomer was collected from the silica gel chromatography in fractions showing a spot of Rf 0.5 on a TLC plate eluted with ether. It was similarly purified (retention time 57–59 minutes), and characterised by mass and nmr spectroscopy, as described in Example 4.

EXAMPLE 12

5-β-Fluoro-25-cyclohexylavermectin B1 monosaccharide and 5-β-fluoro-25-cyclohexylavermectin B1 aglycone (n=1 and n=0 respectively, R$^5$=OH)

5-β-Fluoro-25-cyclohexylavermectin B1 (0.4 g), from Example 11, was dissolved in isopropanol (65 ml) containing 1% v/v concentrated sulphuric acid. The solution was stood at room temperature for 24 hours, then poured into excess sodium hydrogen carbonate solution, and the product extracted with ether. The extracts were dried (MgSO$_4$) and evaporated to a foam. This was purified by chromatography on a 2" Dynamax (trade mark) ODS column eluting with water:methanol 13:87 at 45 ml/minute. The aglycone was eluted first (19 minutes), followed by the title monosaccharide (30–38 minutes). These were characterised by mass and nmr spectroscopy, as described in Example 4.

EXAMPLE 13

5-β-Fluoro-22,23-dihydro-25-cyclohexylavermectin B1

5-β-Fluoro-25-cyclohexylavermectin B1 (0.4 g) from Example 11 and Wilkinson's catalyst (40 mg) were dissolved in toluene (100 ml), purged with nitrogen for 5 minutes, then hydrogenated at 50 psi for 18 hours at room temperature. A further 40 mg of catalyst was added, and hydrogenation continued for 24 hours. A further 100 mg portion of catalyst was added, and hydrogenation continued for a further 3 days. The solution was then heated with thiourea (100 mg) on a steam bath for 5 hours, cooled and filtered through Hyflo (trade mark) and evaporated. The resulting foam was purified on a 2" Dynamax (trade mark) ODS column, eluting with water:methanol 10:90, rising to 5:95 over 60 minutes. The product eluted over 33–44 minutes, and was characterised by mass and nmr spectroscopy, as described in Example 4.

EXAMPLE 13a

5-α-Fluoro-22,23-dihydro-25-cyclohexylavermectin B1

In a similar manner to Example 13, 5-α-fluoro-25-cyclohexylavermectin B1 (0.4 g), from Example 11, was hydrogenated with Wilkinson's catalyst (40 mg) in toluene (100 ml). The product was purified on a 2" Dynamax (trade mark) ODS column, eluting with water:methanol as in Example 13. The product eluted after 33–44 minutes, and was characterized by mass and nmr spectroscopy, as described in Example 4.

EXAMPLE 14

5-Keto-23-O-methyl-25-cyclohexylavermectin B2 ($R^1$=OMe, $R^2$=cyclohexyl, $R^3$=H, $R^4$=H, $R^5$=OH, n=2)

23-O-Methyl-25-cyclohexylavermectin B2 (15 g) (British Patent Application 9201505.6) was suspended in ether (500 ml). Activated manganese dioxide (45 g) was added portionwise over 4 hours whilst the mixture was stirred at room temperature. After 48 hours, further oxidant was added until reaction was judged to be complete by tlc. The suspension was then filtered through Hyflo (trade mark), the inorganic residue washed well with ether, and the combined filtrates evaporated to give the title compound (12 g) as a yellow foam, characterised by mass spectroscopy.

EXAMPLE 15

5-Hydrazono-23-O-methyl-25-cyclohexylavermectin B2

Hydrazine dihydrochloride (12.5 g) and sodium acetate (25 g) were stirred for 40 minutes in a mixture of dichloromethane (400 ml) and glacial acetic acid (10 ml). This mixture was then cooled in ice whilst 5-keto-23-O-methyl-25-cyclohexylavermectin B2 (12 g), from Example 14, was added. The reaction was then stirred for 5 hours, during which time it was allowed to reach room temperature, when tlc showed reaction to be complete. It was then washed twice with water, and then with saturated sodium hydrogen carbonate solution, dried (MgSO$_4$), and evaporated to give the title compound (12.2 g), characterised by mass and nmr spectroscopy. Reverse-phase high performance liquid chromatography showed it to be 85% pure.

EXAMPLE 16

5-Diazo-23-O-methyl-25-cyclohexylavermectin B2

The 5-hydrazono-23-O-methyl-25-cyclohexylavermectin B2 (12.2 g), from Example 15, was dissolved in ether (300 ml) and the solution cooled to 0° C. Activated manganese dioxide (50 g) was added in portions over 10 minutes. The suspension was then stirred at 0° C. for 30 minutes, when tlc indicated reaction was complete. The reaction mixture was filtered through Hyflo (trade mark), and the inorganic residue washed well with ether. The combined filtrates were evaporated to give the title compound as a pink solid (12 g), which was characterised by infra-red and nmr spectroscopy, as described in Example 3. Reverse-phase high performance liquid chromatography analysis showed it to be 90% pure.

EXAMPLE 17

5-β-Fluoro-23-O-methyl-25-cyclohexylavermectin B2 and its 5-α-diastereomer

5-Diazo-23-O-methyl-25-cyclohexylavermectin B2 (12 g), from Example 16, was dissolved in dry ether (500 ml) in a polypropylene tube. Pyridinium poly(hydrogen fluoride) (2.5 ml) was added and the mixture stirred at room temperature overnight. The solution was then washed twice with saturated sodium hydrogen carbonate solution, then with brine. It was dried over sodium sulphate and evaporated to dryness. The resulting yellow solid was then chromatographed over silica gel (250 g), eluting with ether:hexane 1:1. The 5-β-diastereomer was collected as the material with Rf of 0.4 on a TLC plate eluted with ether. A portion (0.4 g) was then purified on a 2" Dynamax (trade mark) ODS hplc column, eluting at 45 ml/minute with water:methanol 12:88 for 30 minutes, then rising to 11:89. The material with retention time of 47–56 minutes was collected, and shown to be the 5-β-diastereomer by mass and nmr spectroscopy, as described in Example 4.

The 5-α-diastereomer was collected from the silica gel chromatography in the fractions showing a spot of Rf 0.5 on a TLC plate eluted with ether. It was similarly purified (retention time 21–27 minutes) and characterise by mass and nmr spectroscopy, as described in Example 4.

EXAMPLE 18

5-β-Fluoro-23-O-methyl-25-cyclohexylavermectin B2 monosaccharide

5-β-Fluoro-23-O-methyl-25-cyclohexylavermectin B2 (1 g) from Example 17 was dissolved in a mixture of isopropanol (60 ml) and concentrated sulphuric acid (0.6 ml). This was stirred at room temperature overnight. It was then poured into excess saturated sodium hydrogen carbonate solution, and the product extracted into ether. The ether extracts were washed with brine, dried (MgSO$_4$) and evaporated to dryness. A portion (0.35 g) of the crude product was purified on a 2" Dynamax (trade mark) ODS column, eluting at 45 ml/minute with water:methanol 12:88. The material with retention time of 28–34 minutes was collected and characterised as the title compound by mass and nmr spectroscopy, as described in Example 4.

EXAMPLE 18a

5-α-Fluoro-23-O-methyl-25-cyclohexylavermectin B2 monosaccharide

This was prepared from 5-α-fluoro-23-O-methyl-25-cyclohexylavermectin B2, from Example 17, as described in Example 18. It was purified on a 2" Dynamax (trade mark) ODS column, eluting at 45 ml/minute with water:methanol 10:90. The product was collected after eluting for 28–34 minutes, and was characterized by mass and nmr spectroscopy, as described in Example 4.

EXAMPLE 19

5-β-Chloro-22,23-dihydro-25-cyclohexylavermectin B1 monosaccharide and its 5-α-diastereomer

15

5-Diazo-22,23-dihydro-25-cyclohexylavermectin B1 monosaccharide (0.5 g), from Example 7, was dissolved in dichloromethane (100 ml) and a saturated solution of anhydrous hydrogen chloride in dichloromethane (2 ml) was added. The mixture was stirred at room temperature for 15 minutes, and was then quenched with saturated sodium hydrogen carbonate solution, the organic phase separated, dried (MgSO$_4$) and evaporated. The crude product was purified on a 2" Dynamax (trade mark) ODS column, eluting with water:methanol:acetonitrile (7:12:81) at 45 ml/minute. The first eluted product was the 5-β-chloro compound, characterized by mass and nmr spectroscopy. Further elution produced the 5-α-diastereomer, characterised in a similar fashion.

EXAMPLE 20

5-α-acetylthio-25-cyclohexylavermectin B2, 3-α-acetylthio-Δ-4,5-25-cyclohexylavermectin B2 and 3-β-acetylthio-25-cyclohexylavermectin B2

5-Diazo-25-cyclohexylavermectin B2 (200 mg) from Example 3 was dissolved in toluene (10 ml) at room temperature, and thiolacetic acid (6 drops) added. The mixture stood until the pink colour was discharged. The solution was then evaporated to dryness. The residue was chromatographed over silica gel, eluting with ether. Appropriate fractions containing materials of Rf.0.3 were pooled, and the products separated by reverse-phase high-performance liquid chromatography on a 2" Dynamax (trade mark) column, eluting first with water:methanol (14:86), and then with water:methanol (12:88). The first two products collected were purified on a 1" Dynamax (trade mark) column, yielding 3-α-acetylthio-Δ-4,5-25-cyclohexylavermectin B2 (25 mg) and a mixture of 5-α-acetylthio-25-cyclohexylavermectin B2 and 3-β-acetylthio-25-cyclohexylavermectin B2 (32 mg). These products were characterised by mass and nmr spectroscopy.

EXAMPLE 21

3-α-methylthio-Δ-4,5-25-cycloavermectin B2 and its 3-β-diastereoisomer

5-Diazo-25-cyclohexylavermectin B2 (200 mg) from Example 3 was dissolved in ether (15 ml) at room temperature, and the solution saturated with methanethiol from a lecture bottle. After six hours, the pink colour had completely disappeared. The solvent was removed by evaporation, and the products isolated by reverse-phase high-performance liquid chromatography on a 2" Dynamax (trade mark) column, eluting with water:methanol:acetonitrile (20:14:66, going to 18:14:68). The α-stereoisomer 3-α-methylthio-Δ-4,5-25-cyclohexylavermectin B2 was eluted first (40 mg), followed by the β-compound 3-β-diastereoisomer. This was rechromatographed on a 1" Dynamax (trade mark) column, eluting water:methanol:acetonitrile 18:14:68), giving 20 mg of pure product. The products 3-α-methylthio-Δ-4,5-25-cyclohexylavermectin B2 and 3-β-diastereoisomer were thus obtained, and characterised by mass and nmr spectroscopy.

EXAMPLE 22

3-α-Mercapto-Δ-4,5-25-cyclohexylavermectin B2 and it 3-β-diastereoisomer

These compounds were obtained by the procedure of Example 21 but using hydrogen sulphide instead of methanethiol. The products were characterised by mass and nmr spectroscopy.

16

EXAMPLE 23

5-α-isocyanato-25-cyclohexylavermectin B2 and its 5-β-diastereoisomer

5-Diazo-25-cyclohexylavermectin B2 (250 mg) from Example 3 was dissolved in ether (5 ml). To this solution was added, in 0.25 ml portions at 10 minute intervals, 1 ml of a solution of thiocyanic acid in toluene. [This was prepared by vigorously stirring a slurry of potassium thiocyanate (0.97 g), potassium hydrogen sulphate (1.37 g) and 5 drops of water, with toluene (10 ml)].

When the pink colour had disappeared, the solution was evaporated to dryness. The products were separated by reverse-phase high-performance liquid chromatography on a 2" Dynamax (trade mark) column, eluting with water:methanol:acetonitrile (18:14:68, going to 18:12:70 after 46 minutes). 5-β-isocyanato-25-cyclohexyl-avermectin B2 (42 mg) was eluted after 61 minutes, followed by its 5-αdiastereoisomer (84 mg) after 68 minutes. The two products were characterised by infra-red, mass and nmr spectroscopy.

EXAMPLE 24

5-Hydrazono-avermectin B1 a

5-Keto-avermectin B1a (0.71 g), prepared as described in Example 1 but starting from avermectin B1a, hydrazine dihydrochloride (0.71 g) and sodium acetate (1.42 g) were combined in dichloromethane (25 ml), and acetic acid (0.5 ml). The mixture was stirred at room temperature for 24 hours. It was then diluted with dichloromethane (25 ml), washed with water and then with aqueous sodium bicarbonate solution, dried over magnesium sulphate, and evaporated to give a foam (625 mg). This was characterized by mass and nmr spectroscopy.

EXAMPLE 25

5-Diazo-avermectin B1a

The hydrazone from Example 20 was dissolved in ether (25 ml), cooled to 0° and activated manganese dioxide (2 g) added. The solution was stirred at 0° for 1 hour, when TLC showed the reaction to be complete. The mixture was filtered through Hyflo (trade mark), washed with ether (25 ml), and the resulting pink solution of the title compound used directly in Example 26.

EXAMPLE 26

5-β-Fluoro-avermectin B1a, and its 5-α-diastereomer

The solution of 5-diazo-avermectin B1a, from Example 25, was cooled to 0° and pyridinium poly(hydrogen fluoride) (0.5 ml) added. The mixture was kept overnight, then worked up as described in Example 4. The crude orange solid was chromatographed over silica gel (100 g), and eluted with hexane:ether (1:1, then 2:3). The eluted product with TLC Rf 0.35 was collected, and purified on a 2" Microsorb (trade mark) column, eluting at 45 ml/minute with water:methanol:acetonitrile 10:13:77. The product which eluted at 17.5–19.5 minutes was shown to be the 5-β-fluoro diastereomer, and was characterized by mass and nmr spectroscopy, as described in Example 4.

The material which eluted from the silica gel column with TLC Rf of 0.5 was similarly purified, and shown to be the 5-α-diastereomer, by mass and nmr spectroscopy, as described in Example 4.

EXAMPLE 27

5-Cyano-Δ-4,5-22,23-dihydro-25-cyclohexylavermectin B1 monosaccharide

5-Diazo-22,23-dihydro-25-cyclohexylavermectin B1 (0.1 g), from Example 7, was dissolved in acetonitrile (25 ml), and copper(I) cyanide (0.2 g) added. The mixture was stirred at room temperature for 24 hours. It was then diluted with ether and the solids filtered off through Hyflo (trade mark). The filtrate was evaporated to a green glass. It was flash-chromatographed through silica gel, eluting with ether, and the product further purified on a 1" Dynamax (trade mark) column, eluting at 20 ml/minute with water:acetonitrile 15:85. Appropriate fractions were pooled, and the title compound obtained as product, characterized by mass, uv and nmr spectroscopy.

EXAMPLE 28

22,23-Dihydro-25-cyclohexylavermectin B1 monosaccharide

25-Cyclohexylavermectin B1 (9.9 g) (see EP 214731) was dissolved in toluene (1 liter) and Wilkinson's catalyst (tristriphenylphosphine rhodium (I) chloride) (9.25 g) was added. The solution was hydrogenated on a large Parr shaker at room temperature at 50 psi hydrogen pressure. After 3 hours the reaction vessel was depressurised and allowed to stand for 12 hours before addition of a further portion of catalyst (5 g) and hydrogenated as before for a further 2 hours after which no starting material remained. The solution was filtered, evaporated to dryness under vacuum and the residue chromatographed on silica eluting with methylene chloride then methylene chloride:methanol 9:1.

The crude product was then chromatographed again on silica (200 g) eluting with methylene chloride:methanol 19:1 to give after evaporation of the solvent under vacuum impure 22,23-dihydro-25-cyclohexylavermectin B1 as a brown foam (10 g). This material was dissolved in a mixture of isopropanol (200 ml) and sulphuric acid (2 ml) and the brown solution was stirred at room temperature for 15 hours then poured into a mixture of ice and water (500 ml) and extracted with methylene chloride (3×200 ml). The organic layer was washed with saturated potassium hydrogen carbonate solution (100 ml), water (2×50 ml) dried over anhydrous magnesium sulphate and evaporated under vacuum to give a crude gum which was chromatographed on silica eluting with methylene chloride then methylene chloride-:ethyl acetate 2:1 to give the title compound (8.2 g). Mass and NMR spectra were fully consistent with the proposed structure.

EXAMPLE 28A

5-Keto-22,23-dihydro-25-cyclohexylavermectin B1 monosaccharide

This was prepared from the monosaccharide described in Example 28, by the method described in Example 1.

EXAMPLE 29

5-β-Thioureido-25-cyclohexylavermectin B2 and its 5-α-diastereomer

A mixture of 5-isothiocyanato-25-cyclohexylavermectin B2 diastereomers (80 mg), prepared as stated in Example 23, was treated with a saturated solution of ammonia in methanol (20 ml). This mixture was stood at room temperature for 2 hours, and then evaporated to dryness. The residue was chromatographed on a 1" Dynamax (trade mark) 5μ ODS column, eluting with water:methanol 16:84. The 5-β-diastereomer of the title compound eluted first, followed by the 5-α-diastereomer. The products were characterized by mass and nmr spectroscopy.

EXAMPLE 30

5-β-N-Methylthioureido-25-cyclohexylavermectin B2 and its 5-α-diastereomer

These were prepared in exactly the same fashion as in Example 29, by addition of methylamine to the 5-isothiocyanates. They were similarly purified by preparative hplc, and characterized by mass and nmr spectroscopy.

EXAMPLE 31

5-β-N,N-Dimethylthioureido-25-cyclohexylavermectin B2 and its 5-α-diastereomer

These were prepared in exactly the same fashion as in Example 29, by addition of dimethylamine to the 5-isothiocyanates. They were similarly purified by preparative hplc, and characterized by mass and nmr spectroscopy.

EXAMPLE 32

3-Keto-5-deoxy-Δ-4,5-25-cyclohexylavermectin B2

5-Diazo-25-cyclohexylavermectin B2 (from Example 3) (300 mg) was dissolved in acetaldehyde (5 ml) and the mixture was kept at room temperature for 2 weeks. Hplc analysis showed some starting material to be present. The acetaldehyde was then removed, and a further 5 ml of aged acetaldehyde was added. After 12 hours, reaction was complete. The solvent was evaporated, and the resulting yellow gum purified on a 2" ODS Dynamax (trade mark) column, eluting with water:acetonitrile:methanol 21:14:65 at 45 ml/minute. The title compound was eluted at 49–53 minutes. Its structure was established by mass, nmr and infrared spectroscopy.

EXAMPLE 33

3-Oximino-5-deoxy-Δ-4,5-25-cyclohexylavermectin B2

The ketone from Example 32 (20 mg) was dissolved in pyridine (1 ml) and hydroxylammonium chloride (60 mg) added. The mixture was left at room temperature for 2 days, then evaporated to dryness. The residue was extracted three times with ether, and the extracts blown down to 1 ml volume. This solution was passed down a Sep Pak (trade mark) silica gel filter, and 10 ml of eluant collected and evaporated to give a yellow gum. This was purified on a 5p Microsorb (trade mark) ODS 1" Dynamax (trade mark) column, eluting with water:acetonitrile:methanol 22:14:64 at 20 ml/minute. The title compound was collected, and its structure was established by mass and nmr spectroscopy.

EXAMPLE 34

3-Methoximino-5-deoxy-Δ-4,5-25-cyclohexylavermectin B2

This was prepared according to the method of Example 33, using methoxyammonium chloride. Reaction was complete in 3 days. The pyridine was evaporated and the residue was purified on a 8μ ODS 1" Dynamax (trade mark) column, eluting with water:methanol 14:86 at 20 ml/minute. The title compound was eluted between 31 and 44 minutes, and its structure was established by mass and nmr spectroscopy.

I claim:
1. A compound of formula (I):

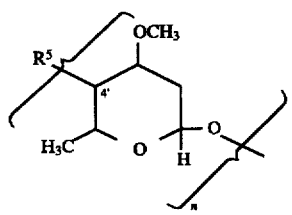

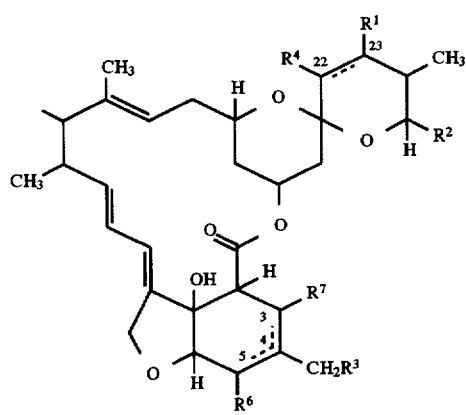

(I)

wherein the broken line at the 22–23 position represents an optional bond and either this bond is present and $R^1$ and $R^4$ are absent or this bond is absent and $R^1$ and $R^4$ are independently H, $OR^8$ wherein $R^8$ is H, $C_1$–$C_8$ alkyl, $C_1$–$C_8$ alkenyl, aralkyl, $C_2$–$C_8$ alkanoyl, $C_3$–$C_8$ alkenoyl, aralkanoyl, aroyl, optionally substituted carbamoyl, optionally substituted methylene, oxo or optionally O-substituted oximino;

$R^2$ is:
  (a) an alpha-branched $C_3$–$C_8$ alkyl, alkenyl, alkoxyalkyl, or alkylthioalkyl group; an alpha-branched $C_4$–$C_8$ alkynyl group; a ($C_5$–$C_8$ cycloalkyl) alkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or
  (b) a group of the formula —$CH_2R^9$ wherein $R^9$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group, wherein any of said alkyl, alkoxy, alkenyl or alkynyl groups may be substituted by one or more halo atoms; or a $C_2$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or a group of the formula $SR^{10}$ wherein $R^{10}$ is $C_1$–$C_8$ alkyl, $C_2$–$C_8$ alkenyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo;

or a 3 to 6 membered oxygen or sulphur containing heterocyclic ring which may be saturated, or fully or partially unsaturated and which may optionally be substituted by one or more $C_1$–$C_4$ alkyl groups or halo atoms; or
  (c) a $C_1$–$C_6$ alkyl group substituted by one oxo or one or more hydroxy groups or by a single oxygen atom on two adjacent carbon atoms forming an oxirane ring, or $R^2$ is a $C_1$–$C_5$ alkyl group substituted by a $C_1$–$C_6$ alkoxycarbonyl group, said substituents on $R^2$ being attached to either or both of a terminal carbon atom and a carbon atom adjacent a terminal carbon atom of $R^2$; or
  (d) =$CH_2$ or a group of the formula:

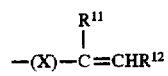

wherein $R^{11}$ and $R^{12}$ are both H; $R^{11}$ is H and $R^{12}$ is $C_1$–$C_8$ alkyl, or one of $R^{11}$ and $R^{12}$ is H and the other is phenyl, heteroaryl, $C_2$–$C_6$ alkoxycarbonyl or substituted phenyl or heteroaryl wherein said substituent is fluorine, chlorine, $C_1$–$C_4$ alkyl, $C_1$–$C_4$ alkoxy, $C_1$–$C_4$ alkylthio, hydroxy ($C_1$–$C_4$)alkyl, cyano, aminosulphonyl, $C_2$–$C_6$ alkanoyl, $C_2$–$C_6$ alkoxycarbonyl, nitro, trifluoromethyl, trifluoromethoxy, amino or mono or di-($C_1$–$C_4$ alkyl)amino; and X is a direct bond or is an alkylene group having from 2 to 6 carbon atoms which may be straight or branched-chain; or
  (e) phenyl which may optionally be substituted with at least one substituent selected from $C_1$–$C_4$ alkyl, $C_1$–$C_4$ alkoxy and $C_1$–$C_4$ alkylthio groups, halo atoms, trifluoromethyl, and cyano; or
  (f) $R^2$ may be a group of formula (II):

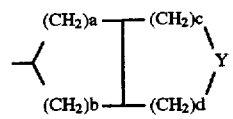

wherein Y is O, S or —$CH_2$— and a, b, c and d may each independently be 0, 1 or 2; the sum of a, b, c and d not exceeding 5;

$R^3$ is H, $OR^8$ where $R^8$ is as defined above, or $R^8$ is a halogen atom; n is 0, 1 or 2;

$R^5$ is attached by a single bond and is H, $OR^8$ where $R^8$ is as defined above, a halogen atom, amino, N-loweralkylamino, N,N-diloweralkylamino, N-loweralkanoylamino, N,N-diloweralkanoylamino, triloweralkylsilyloxy, —$S(O)_mR^{13}$ where m is 0, 1 or 2, or —$SCOR^{13}$ wherein $R^{13}$ is H or an optionally substituted alkyl, cycloalkyl or aryl group;

or $R^5$ is attached by a double bond and is oxo, or an optionally substituted oximino, semicarbazono, thiosemicarbazono or hydrazono group; or $R^5$ represents OH, both of which are attached by a single bond. $R^{14}$ being an optionally substituted $C_1$–$C_8$ alkyl, $C_2$–$C_8$ alkenyl or aryl group, the broken lines between the 3–4 and 4–5 positions represent optional bends and either:
  (i) the 3–4 optional bond is present, the 4–5 optional bond is absent, $R^7$ is absent and $R^8$ is a β-halogen atom, an isothiocyanate group, a thioureido group of formula $NHCSNR^{15}R^{16}$ where $R^{15}$ and $R^{16}$ are independently H, $C_1$–$C_8$ alkyl, cycloalkyl, aryl or aralkyl groups, an azido group or a $C_1$–$C_8$ alkylcarbonylthio-group, or (ii) the 4–5 optional bond is present, the 3–4 optional bond is absent, $R^6$ is absent and $R^7$ is a mercapto, $C_1$–$C_8$ alkylthio, or $C_1$–$C_8$ alkylcarbonylthio group; or $R^7$ is absent and $R^6$ is CN;

with the proviso that:

(a) when $R^2$ does not represent $CH(CH_3)_2$, $CH(CH_3)(C_2H_5)$, $C(CH_3)=CH(CH_3)$, $C(CH_3)=CH(C_2H_5)$ or $C(CH_3)=CHCH(CH_3)_2$;

(b) when $R^1$ and $R^4$ each represent H; $R^2$ represents $CH(CH_3)(C_2H_5)$; $R^3$ represents H; $R^5$ represents OH; and $R^6$ represents α-Cl or α-Br; then n does not represent 2; and (c) when $R^1$ represents H or OH; $R^2$ represents $C(CH_3)=CHCH(CH_3)_2$; $R^3$, $R^4$ and $R^5$ each represent H; and $R^6$ represents α-Cl; then n does not represent 0.

2. A compound according to claim 1 in which $R^2$ is am alkyl or cycloalkyl group.

3. A compound according to claim 2, in which $R^2$ is cyclohexyl, isopropyl or sec-butyl.

4. A compound according to claim 1, in which $R^3$ is H and the optional bond at the 22–23 position is present or this optional bond is absent and $R^1$ is H or OH.

5. A compound according to claim 1 in which $R^3$ and $R^4$ are H.

6. A compound according to any preceding claim where $R^6$ is a β-halogen atom.

7. A compound according to claim 1 where $R^6$ is β-fluoro.

8. Any one of the following compounds:

5-β-fluoro-25-cyclohexylavermectin B2;

5-β-fluoro-25-cyclohexylavermectin B2 monosaccharide (n=1);

5-β-fluoro-22,23-dihydro-25-cyclohexylavermectin B1 monosaccharide (n=1);

5-β-fluoro-25-cyclohexylavermectin B1;

5-β-fluoro 25-cyclohexylavermectin B1 aglycone (n=0);

5-β-fluoro-22,23-dihydro-25-cyclohexylavermectin B1;

5-β-fluoro-23-0-methyl-25-cyclohexylavermectin B2;

5-β-fluoro-23-0-methyl-25-cyclohexylavermectin B2 monosaccharide;

5-β-chloro-22,23-dihydro-25-cyclohexylavermectin B1 monosaccharide;

5-β-fluoro-avermectin B1 a.

9. A pharmaceutical or veterinary composition, comprising a compound of formula I, as defined in claim 1, but without provisos (b) and (c), and a pharmaceutically acceptable carrier or excipient.

10. A compound of the formula:

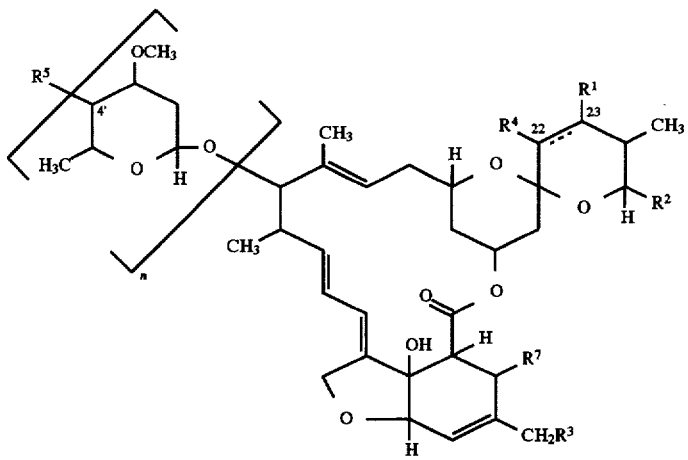

wherein the broken line at the 22–23 position represents an optional bond and either this bond is present and $R^1$ and $R^4$ are absent or this bond is absent and $R^1$ and $R^4$ are independently H, $OR^8$ wherein $R^8$ is H, $C_1$–$C_8$ alkyl, $C_1$–$C_8$ alkenyl, aralkyl, $C_2$–$C_8$ alkanoyl, $C_3$–$C_8$ alkenoyl, aralkanoyl, aroyl, optionally substituted carbamoyl, optionally substituted methylene, oxo or optionally O-substituted oximino;

$R^2$ is:

(a) an alpha-branched $C_3$–$C_8$ alkyl, alkenyl, alkoxyalkyl, or alkylthioalkyl group; an alpha-branched $C_4$–$C_8$ alkynyl group; a ($C_5$–$C_8$ cycloalkyl) alkyl group wherein the alkyl group is an alpha-branched $C_2$–$C_8$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or (b) a group of the formula —$CH_2R^9$ wherein $R^9$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group, wherein any of said alkyl, alkoxy, alkenyl or alkynyl groups may be substituted by one or more halo atoms; or a $C_2$–$C_8$ cycloalkyl or $C_5$–$C_8$ cycloalkenyl group, either or which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or a group of the formula $SR^{10}$ wherein $R^{10}$ is $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo; or a 3 to 6 membered oxygen or sulphur containing heterocyclic ring which may be saturated, or fully or partially unsaturated and which may optionally be substituted by one or more $C_1$–$C_4$ alkyl groups or halo atoms; or (c) a $C_1$–$C_6$ alkyl group substituted by one oxo or one or more hydroxy groups or by a single oxygen atom on two adjacent carbon atoms forming an oxirane ring, or $R^2$ is a $C_1$–$C_5$ alkyl group substituted by a $C_1$–$C_6$ alkoxycarbonyl group, said substituents on $R^2$ being attached to either or both of a terminal carbon atom and a carbon atom adjacent a terminal carbon atom of $R^2$; or (d) =$CH_2$ or a group of the formula:

wherein $R^{11}$ and $R^{12}$ are both H; $R^{11}$ is H and $R^{12}$ is $C_1$–$C_8$ alkyl, or one of $R^{11}$ and $R^{12}$ is H and the other is phenyl, heteroaryl, $C_2$–$C_6$ alkoxycarbonyl or substituted phenyl or heteroaryl wherein said substituent is fluorine, chlorine, $C_1$–$C_4$ alkyl, $C_1$–$C_4$ alkoxy, $C_1$–$C_4$ alkylthio, hydroxy ($C_1$–$C_4$) alkyl, cyano, aminosulphonyl, $C_2$–$C_6$ alkanoyl, $C_2$–$C_6$ alkoxycarbonyl, nitro, trifluoromethyl, trifluoromethoxy, amino or mono or di-($C_1$–$C_4$ alkyl)amino; and X is a direct bond or is an alkylene group having from 2 to 6 carbon atoms which may be straight or branched-chain; or (e) phenyl which may optionally be substituted with at least one substituent selected from $C_1$–$C_4$ alkyl, $C_1$–$C_4$ alkoxy and $C_1$–$C_4$ alkylthio groups, halo atoms, trifluoromethyl, and cyano; or (f) $R^2$ may be a group of formula (II):

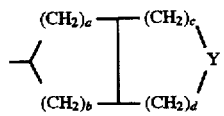

wherein Y is O, S or —$CH_2$— and a, b, c and d may each independently be 0, 1 or 2; the sum of a, b, c and d not exceeding 5;

$R^3$ is H, $OR^8$ where $R^8$ is as defined above, or $R^3$ is a halogen atom; n is 0, 1 or 2;

$R^5$ is attached by a single bond and is H, $OR^8$ where $R^8$ is as defined above, a halogen atom, amino, N-loweralkylamino, N,N-diloweralkylamino, N-loweralkanoylamino, N,N-diloweralkanoylamino, triloweralkylsilyloxy, -S(O)m$R^{13}$ where m is 0, 1 or 2 or —SCO$R^{13}$ wherein $R^{13}$ is H or an optionally substituted $C_1$–$C_8$ alkyl, cycloalkyl or aryl group;

or $R^5$ is attached by a double bond and is oxo, or an optionally substituted oximino, semicarbazono, thiosemicarbazono or hydrazono group; or $R^5$ represents OH, $R^{14}$ both of which are attached by a single bond, $R^{14}$ being an optionally substituted $C_1$–$C_8$ alkyl, $C_2$–$C_8$ alkenyl or aryl group; and $R^7$ is oxo or optionally substituted imino.

11. A compound of the formula:

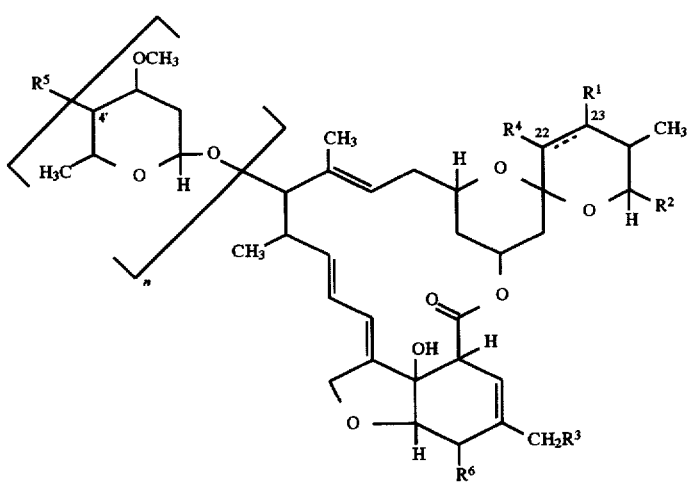

wherein the broken line at the 22–23 position represents an optional bond and either this bond is present and $R^1$ and $R^4$ are absent or this bond is absent and $R^1$ and $R^4$ are independently H, $OR^8$ wherein $R^8$ is H, $C_1$–$C_8$ alkyl, $C_1$–$C_8$ alkenyl, aralkyl, $C_2$–$C_8$ alkanoyl, $C_3$–$C_8$ alkenoyl, aralkanoyl, aroyl, optionally substituted carbamoyl, optionally substituted methylene, oxo or optionally O-substituted oximino;

$R^2$ is:

(a) an alpha-branched $C_3$–$C_8$ alkyl, alkenyl, alkoxyalkyl, or alkylthioalkyl group; an alpha-branched $C_4$–$C_8$ alkynyl group; a ($C_5$–$C_8$ cycloalkyl) alkyl group wherein the alkyl group is an alpha-branched $C_2$–$C_8$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or (b) a group of the formula —$CH_2R^9$ wherein $R^9$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group, wherein any of said alkyl, alkoxy, alkenyl or alkynyl groups may be substituted by one or more halo atoms; or a $C_2$–$C_8$ cycloalkyl or $C_5$–$C_8$ cycloalkenyl group, either or which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms; or a group of the formula $SR^{10}$ wherein $R^{10}$ is $C_1-C_8$ alkyl, $C_2-C_8$ alkenyl, $C_2-C_8$ alkynyl, $C_3-C_8$ cycloalkyl, $C_5-C_8$ cycloalkenyl, phenyl or substituted phenyl wherein the substituent is $C_1-C_4$ alkyl, $C_1-C_4$ alkoxy or halo; or a 3 to 6 membered oxygen or sulphur containing heterocyclic ring which may be saturated, or fully or partially unsaturated and which may optionally be substituted by one or more $C_1-C_4$ alkyl groups or halo atoms; or (c) a $C_1-C_6$ alkyl group substituted by one oxo or one or more hydroxy groups or by a single oxygen atom on two adjacent carbon atoms forming an oxirane ring, or $R^2$ is a $C_1-C_5$ alkyl group substituted by a $C_1-C_6$ alkoxycarbonyl group, said substituents on $R^2$ being attached to either or both of a terminal carbon atom and a carbon atom adjacent a terminal carbon atom of $R^2$; or (d) =$CH_2$ or a group of the formula:

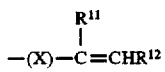

wherein $R^{11}$ and $R^{12}$ are both H; $R^{11}$ is H and $R^{12}$ is $C_1-C_8$ alkyl, or one of $R^{11}$ and $R^{12}$ is H and the other is phenyl, heteroaryl, $C_2-C_8$ alkoxycarbonyl or substituted phenyl or heteroaryl wherein said substituent is fluorine, chlorine, $C_1-C_4$ alkyl, $C_1-C_4$ alkoxy, $C_1-C_4$ alkylthio, hydroxy $(C_1-C_4)$alkyl, cyano, aminosulphonyl, $C_2-C_8$ alkanoyl, $C_2-C_8$ alkoxycarbonyl, nitro, trifluoromethyl, trifluoromethoxy, amino or mono or di-$(C_1-C_4$ alkyl)amino; and X is a direct bond or is an alkylene group having from 2 to 6 carbon atoms which may be straight or branched-chain; or (e) phenyl which may optionally be substituted with at least one substituent selected from $C_1-C_4$ alkyl, $C_1-C_4$ alkoxy and $C_1-C_4$ alkylthio groups, halo atoms, trifluoromethyl, and cyano; or (f) $R^2$ may be a group of formula (II):

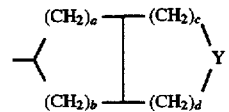

wherein Y is O, S or —$CH_2$— and a, b, c and d may each independently be 0, 1 or 2; the sum of a, b, c and d not exceeding 5;

$R^3$ is H, $OR^8$ where $R^8$ is as defined above, or $R^3$ is a halogen atom; n is 0, 1 or 2;

$R^5$ is attached by a single bond and is H, $OR^8$ where $R^8$ is as defined above, a halogen atom, amino, N-loweralkylamino, N,N-diloweralkylamino, N-loweralkanoylamino, N,N-diloweralkanoylamino, triloweralkylsilyloxy, —$S(O)mR^{13}$ where m is 0, 1 or 2 or —$SCOR^{13}$ wherein $R^{13}$ is H or an optionally substituted $C_1-C_8$ alkyl, cycloalkyl or aryl group;

or $R^5$ is attached by a double bond and is oxo, or an optionally substituted oximino, semicarbazono, thiosemicarbazono or hydrazono group; or $R^5$ represents OH, $R^{14}$ both of which are attached by a single bond, $R^{14}$ being an optionally substituted $C_1-C_8$ alkyl, $C_2-C_8$ alkenyl or aryl group; and $R^6$ is a diazo group.

12. A method of treatment or prophylaxis of parasitic infections, which comprises administering to an animal or human an effective amount of a compound of formula I, as defined in claim 1, but without provisos (b) and (c).

13. A process for preparing a compound according to claim 1, whereby a compound of claim 11 is reacted with a nucleophilic species.

14. A process according to claim 13, where the nucleophilic species is selected from fluoride, chloride, thiolacetate, methanethiolate, thiolate, thiocyanate or cyanide.

15. A process whereby a compound of claim 11 is reacted with an aldehyde.

16. A process whereby a hydrazone-substituted avermectin or milbemycin derivative is oxidized to give a diazo-substituted avermectin or milbemycin derivative.

* * * * *